US008662076B2

(12) United States Patent
Kuehn et al.

(10) Patent No.: US 8,662,076 B2
(45) Date of Patent: Mar. 4, 2014

(54) TWO-PART CAPSULE WITH PRE-CLOSURE FOR HOUSING PHARMACEUTICAL PREPARATIONS FOR POWDER INHALERS

(75) Inventors: Torsten Kuehn, Appenheim (DE); Rolf Kuhn, Ingelheim (DE); Burkhard Metzger, Ingelheim (DE); Hubert Hoelz, Oberheimbach (DE); Stefan Lustenberger, Gensingen (DE); Herbert Wachtel, Ingelheim (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 1437 days.

(21) Appl. No.: 11/327,050

(22) Filed: Jan. 6, 2006

(65) Prior Publication Data

US 2006/0157054 A1    Jul. 20, 2006

(30) Foreign Application Priority Data

Jan. 11, 2005    (DE) .......................... 10 2005 001 332

(51) Int. Cl.
*A61M 15/00* (2006.01)
*A61J 1/00* (2006.01)
*A61K 9/48* (2006.01)
*B65D 6/00* (2006.01)

(52) U.S. Cl.
USPC ............ 128/200.24; 128/203.12; 128/203.15; 128/203.21; 424/451; 424/453; 220/8; 206/528; 206/530

(58) Field of Classification Search
USPC ............. 128/200.24, 203.15, 203.12, 203.21; 424/451, 453; 206/115, 226, 459, 525, 206/528, 530, 534, 539, 807, 220, 291, 206/292; 220/8
See application file for complete search history.

(56) References Cited

U.S. PATENT DOCUMENTS

| 596,591 A | 1/1898 | Higgins |
| 2,718,980 A * | 9/1955 | Strom .......................... 220/780 |
| 3,159,545 A | 12/1964 | Kidwell |
| 3,285,408 A | 11/1966 | Carnaghi |
| 3,623,997 A | 11/1971 | Powell |

(Continued)

FOREIGN PATENT DOCUMENTS

| CA | 2 338 323 A1 * | 2/2000 |
| DE | 1516488 A1 | 1/1970 |

(Continued)

OTHER PUBLICATIONS

Ansel, H.C. Introduction to Pharmaceutical Dosage Forms, 4th Ed., 1985, Lea & Febiger, Philadelphia, pp. 128-131.*

(Continued)

*Primary Examiner* — Justine Yu
*Assistant Examiner* — Valerie L Skorupa
(74) *Attorney, Agent, or Firm* — Michael P. Morris; Wendy A. Petka

(57) ABSTRACT

The present invention relates to capsules for housing pharmaceutical preparations for powder inhalers with increased medicinal product safety and capsules for pharmaceutical preparations for powder inhalers with improved adaption to use in powder inhalers. The capsules consist of non-water-soluble, hydrophobic plastics, which themselves do not substantially influence the pharmaceutical quality of the contents, but improve the usability of the filled capsules in respect of their operation, the period of use and/or the geographical location of their use and are advantageous in various steps from manufacture to use.

15 Claims, 2 Drawing Sheets

(56) References Cited

U.S. PATENT DOCUMENTS

| | | | |
|---|---|---|---|
| 3,664,495 A * | 5/1972 | Graham et al. | 220/8 |
| 3,807,400 A | 4/1974 | Cocozza | |
| 3,823,843 A * | 7/1974 | Stephens et al. | 424/454 |
| 3,949,751 A | 4/1976 | Birch | |
| 3,991,761 A | 11/1976 | Cocozza | |
| 4,040,536 A * | 8/1977 | Schwarz | 220/8 |
| 4,069,819 A | 1/1978 | Valentini et al. | |
| 4,192,309 A | 3/1980 | Paulsen | |
| 4,196,565 A * | 4/1980 | Bodenmann et al. | 53/471 |
| 4,210,140 A | 7/1980 | James et al. | |
| 4,353,365 A | 10/1982 | Hallworth et al. | |
| 4,489,327 A * | 12/1984 | Eastwell | 342/432 |
| 4,533,542 A | 8/1985 | Buddenbaum et al. | |
| 4,535,567 A * | 8/1985 | Seaborn | 451/317 |
| 4,648,532 A | 3/1987 | Green | |
| 4,656,066 A * | 4/1987 | Wittwer | 428/34.1 |
| 4,667,498 A | 5/1987 | Sauter | |
| 4,692,314 A | 9/1987 | Kenji | |
| 4,738,724 A | 4/1988 | Wittwer et al. | |
| 4,792,451 A * | 12/1988 | Kim | 424/453 |
| 4,793,493 A | 12/1988 | Makiej, Jr. | |
| 4,860,740 A | 8/1989 | Kirk | |
| 4,863,017 A | 9/1989 | Vlock | |
| 4,880,547 A | 11/1989 | Kenji | |
| 4,883,182 A | 11/1989 | Hughes | |
| 4,889,114 A | 12/1989 | Kladders | |
| 4,892,766 A | 1/1990 | Jones | |
| 4,893,721 A * | 1/1990 | Bodenmann et al. | 220/8 |
| 5,152,284 A * | 10/1992 | Valentini et al. | 128/203.21 |
| 5,223,265 A | 6/1993 | Wong | |
| 5,283,064 A | 2/1994 | Suzuki | |
| 5,342,624 A | 8/1994 | McNeill et al. | |
| 5,370,879 A | 12/1994 | Masterson et al. | |
| 5,388,698 A | 2/1995 | Wakao | |
| 5,396,986 A | 3/1995 | Fountain et al. | |
| 5,498,255 A * | 3/1996 | Wong | 604/892.1 |
| 5,575,398 A | 11/1996 | Robbins, III | |
| 5,587,177 A * | 12/1996 | Grimberg | 424/454 |
| 5,632,971 A * | 5/1997 | Yang | 428/34.1 |
| 5,641,510 A * | 6/1997 | Clark et al. | 424/451 |
| 5,673,686 A | 10/1997 | Villax et al. | |
| 5,685,294 A | 11/1997 | Gupte et al. | |
| 5,750,143 A * | 5/1998 | Rashid et al. | 424/451 |
| 5,752,505 A * | 5/1998 | Ohki et al. | 128/203.15 |
| 5,770,224 A | 6/1998 | Rashid et al. | |
| 5,795,591 A | 8/1998 | Lee et al. | |
| 5,881,721 A | 3/1999 | Bunce et al. | |
| 5,947,118 A | 9/1999 | Hochrainer et al. | |
| 6,488,027 B1 | 12/2002 | Moulin | |
| 6,762,005 B2 | 7/2004 | Katano et al. | |
| 6,941,954 B1 * | 9/2005 | Belcher | 132/73 |
| 6,941,980 B2 | 9/2005 | Rocchio et al. | |
| 6,949,154 B2 | 9/2005 | Hochrainer et al. | |
| 7,252,087 B2 * | 8/2007 | Wachtel | 128/203.21 |
| 7,284,553 B2 * | 10/2007 | Hochrainer | 128/203.21 |
| 2001/0008637 A1 * | 7/2001 | Hochrainer et al. | 424/451 |
| 2003/0106827 A1 | 6/2003 | Cheu et al. | |
| 2003/0183548 A1 | 10/2003 | Oertel | |
| 2004/0025876 A1 | 2/2004 | Miller et al. | |
| 2004/0131668 A1 | 7/2004 | Hochrainer et al. | |

FOREIGN PATENT DOCUMENTS

| | | |
|---|---|---|
| DE | 33 45 722 A1 | 6/1985 |
| DE | 4318455 A1 | 12/1994 |
| EP | 0110500 A1 | 6/1984 |
| EP | 0 143 524 | 6/1985 |
| EP | 0 147 755 A2 | 7/1985 |
| EP | 0460921 A2 | 12/1991 |
| EP | 0597136 A1 | 5/1994 |
| EP | 1100474 A2 | 5/2001 |
| FR | 2 380 032 A1 | 9/1978 |
| GB | 691696 A | 5/1953 |
| GB | 938828 A | 10/1963 |
| GB | 2 064 336 A | 6/1981 |
| JP | 5352619 A | 5/1978 |
| JP | 5271055 A | 10/1993 |
| JP | 7118143 A | 5/1995 |
| JP | 3028641 U | 9/1996 |
| JP | 8229101 A | 9/1996 |
| JP | 9104060 A | 4/1997 |
| JP | 9193963 A | 7/1997 |
| JP | 10-502283 A | 3/1998 |
| WO | 82 01470 A1 | 5/1982 |
| WO | 9428958 A1 | 12/1994 |
| WO | 9601105 A1 | 1/1996 |

OTHER PUBLICATIONS

M Matumoto et al., ed. >>Pharmaceutics Manual, 1st ed., Nanzando, p. 123, 1989.

Kirk-Othmer encyclopedia of Chemical Technology, Ed. M. Howe-Grant, p. 729, 1996.

Okano ed., "New General, Pharmaceutics", revised 3rd ed.,Nanzando, p. 367, 1987.

Slepian, β3-Integrins Rather than β-Integrins Dominate Interfin-Matrix Interactions Involved in Postingury Smooth Muscle Cell Migration, American Heart Association,; 97: pp. 1818-1827, May 12, 1998.

Brandrup. J. & Immergut, E.H., Polymer Handbook, pp. 436-437, copyright 1989, Third Edition, John Wiley & Sons, U.S.

* cited by examiner

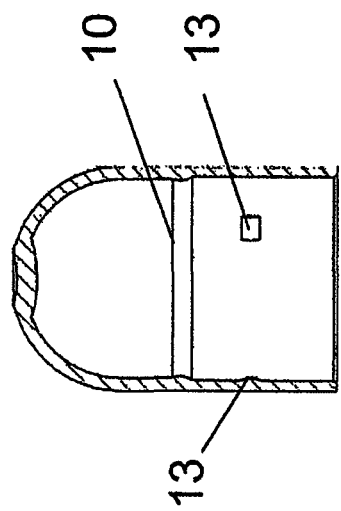
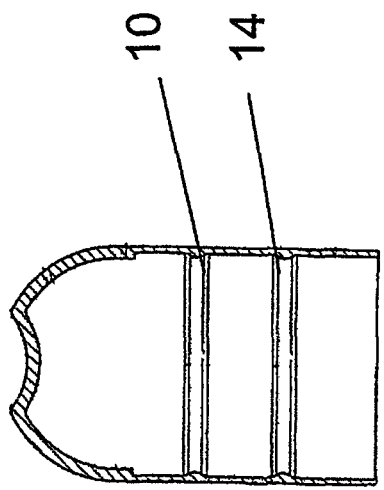
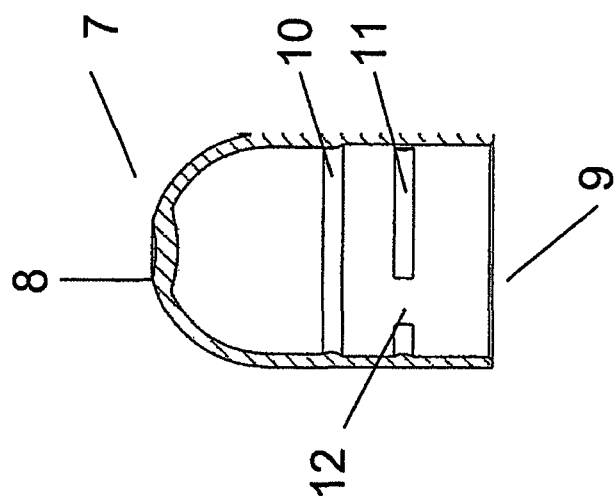
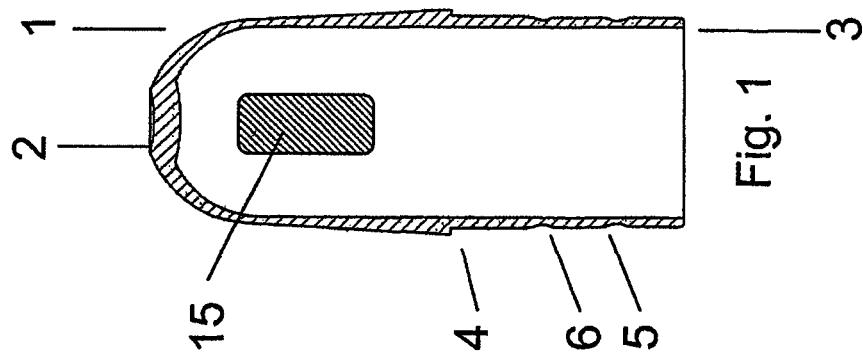

TWO-PART CAPSULE WITH PRE-CLOSURE FOR HOUSING PHARMACEUTICAL PREPARATIONS FOR POWDER INHALERS

The invention relates to novel two-part capsules for housing pharmaceutical preparations for use in powder inhalers which have a main closure and a pre-closure.

State of the Art

Capsules with pharmaceutical preparations are used in various ways in the therapy and diagnosis of diseases. The capsules can be administered orally or are used in specific medical devices such as powder inhalers. Generally, the capsules consist of two parts, a capsule body (body) and a capsule top (top) which can be pushed telescopically into each other. However, multi-part capsules are also known. The capsules consist in most cases of gelatin, in particular hard gelatin. For some special applications the capsules sometimes also consist of water-soluble plastics easily digestible for humans, in order e.g. to release the active ingredient in specific compartments of the gastrointestinal tract in oral administration.

EP 1100474 discloses plastic capsules which consist of a capsule body and a capsule top both of which consist of the same non-water-soluble, hydrophobic plastic and which can be joined to each other such that a stable, sealed-off cavity of defined volume is formed. The plastic is in particular polyethylene. The capsule can have locking elements which firmly join the capsule top to the capsule body. The capsules are intended for use in powder inhalers. The present invention relates to a further development of these capsules. Therefore reference is explicitly made here to the whole of the content of EP 1100474.

Accordingly the capsules according to the invention are also proposed and suitable for use for all types of powder inhaler which operate with capsules as active ingredient reservoir. As an example of such powder inhalers there may be named: inhalers such as are known under the brand names Spinhaler®, Rotahaler®, Aerolizer®, Flowcaps®, Turbospin®, AIR DPI®, Orbital®, Directhaler® and/or are described in DE 33 45 722, EP 0 591 136, DE 43 18 455, WO 91/02558, FR-A-2 146 202, U.S. Pat. No. 4,069,819, EP 666085, EP 869079, U.S. Pat. No. 3,991,761, WO99/45987. However, the capsules are particularly proposed for use in an inhaler of the HandiHaler® brand, as disclosed e.g. in EP 1342483.

The appliance of the HandiHaler® brand is an inhaler in which the Bernoulli principle is applied. A common feature of Bernoulli inhalers that the active ingredient to be dispensed is housed in a cylindrical capsule and this capsule is inserted in a capsule chamber of the inhaler. The capsule chamber is in most cases also formed cylindrical, being somewhat longer and somewhat larger in diameter than the capsule, so that the capsule can vibrate in it both vertically (=axially) and horizontally (=radially), while remaining aligned essentially parallel to the chamber axis. The capsule chamber has an air inlet in the area of one of the two ends and an air outlet in the area of the other end. The air outlet (air duct) leads to a mouthpiece. Within the framework of the present description of the invention the direction stretching from the capsule chamber via the air duct to the mouthpiece defines the longitudinal axis and thus the axial direction. The direction perpendicular thereto defines the vertical or radial direction.

To dispense the active capsule content, the capsule is firstly opened customarily in two places on the long-side casing. Generally the openings are in the vicinity of the two long-side ends of the capsule. If an air flow from the air inlet to the air outlet is now created in the capsule chamber this leads along the longitudinal axis of the capsule with a two-fold effect: firstly the capsule is moved by the air flow mainly along its longitudinal axis. It can also vibrate in a small area. Secondly, the air flowing along by the two capsule openings creates a negative pressure vis-à-vis the inside of the capsule so that the powder in the capsule is carried along by the air flow and atomized.

The capsules customarily used for such inhalers consist of two cup-like parts which can be inserted telescopically into each other. The outer form of a capsule assembled in this way is that of a sealed cylinder with hemispherical ends. The cylinder has a longitudinal axis and a transverse axis. The longitudinal axis is the axis which lies parallel to the generatrix of the cylinder casing. The longitudinal axis is longer than the transverse axis, so that the longitudinal section of the capsule has an oval, and the cross-section a circular, geometry.

The HandiHaler® already mentioned and preferred within the framework of the present invention consists of a) a cup-shaped lower part open to the top, b) a panel which covers the opening of the lower part and perpendicular to which is formed a capsule chamber of the type described above, a button movable towards a spring being provided in the capsule chamber, and having two ground needles for opening the capsule, c) an upper part with a mouth tube which—being able to conduct a powder aerosol—is connected to the capsule chamber and d) a top. The elements a), b) c) and d) are connected to each other by a common hinge element so that they can be moved foldable against each other.

Additionally this patent application describes a capsule holder, which can be formed as a hole in the panel b) and having ribs at the edge. The capsule is clamped into this capsule holder for the purpose of stocking-up.

Further Bernoulli inhalers are disclosed in DE 3345722 and WO 91/02558.

During the production and subsequent filling of capsules according to EP 1100474, the capsules are firstly produced by machine, provisionally closed, then transported to the filling units, where they are re-opened, filled and finally closed definitively. The capsule top is generally fitted loosely onto the capsule body for the provisional closure. During the following procedure it may however happen that the capsule top falls off the capsule body or opens so that contamination of the inside of the capsule becomes possible. Such opened or contaminated capsules must then be removed before the filling procedure with the pharmaceutical formulation.

DESCRIPTION OF THE INVENTION

The present invention solves this problem by creating a capsule of the type described above which, in addition to a final closure means, the main closure, also has a provisional closure means, the pre-closure.

Therefore an object of the present invention is to create capsules which can be produced easily, can easily be provisionally closed but easily reopened again, and which can finally also be closed so that they can preferably be opened again only by damaging the capsule.

A further object of the invention is to create such capsules in which as few structure elements as possible must be formed on the capsule top or the capsule body for the provisional closure and the final closure.

Another object is to create such a capsule in which no preferential pre-orientation between capsule body and capsule top, beyond a simple assembly of the two part elements over the area of same, open in each case, is necessary for the provisional and/or final closure of the capsule.

DETAILED DESCRIPTION OF THE INVENTION

The capsule according to the invention consists of two parts, a capsule body (body) and a capsule top (top) which can be joined to each other so that that a stable, sealed cavity of defined volume is formed which contains the pharmaceutical formulation. The size of the capsule is such that it can be used in current powder inhalers fitted with capsules, as described e.g. in patent specifications DE 33 45 722 (Ingelheim M Inhaler), EP 0 591 136 (Ingelheim Inhaler) or in EP 1342483 (HandiHaler®).

The casings of the top and body describe a hollow cylinder with round cross-section, the top side in each case being open and the under side closed. The closed capsule is thus conical on the outside and cylindrical on the inside. The closed under side can be flat or convex or have another tool-specific shape. The elongation of the closed capsule (distance from the closed end of the body to the closed end of the top in relation to the greatest diameter of the closed capsule) is greater than 1.

There come into consideration as plastic material for the capsule all pharmaceutically permissible plastics which can be processed by injection or blow moulding and thermoforming and/or plastics, the processing of which to produce the capsule top or capsule body requires no mould release agent that can cause the contents to stick to the capsule wall. The plastic should also display no marked adhesion for pharmaceutical-chemical substances, in particular for particles of respirable size. The preferred Shore D hardness of the materials lies between 10 and 85, preferably between 55 and 75, particularly preferably 60 and 70. The material should also be such that a plastic capsule withstands a force of up to 20 N along the longitudinal axis. Also, the wall of the capsule should display a water-vapour permeability of less than $1.3 \times 10^{-14}$ kg/(m² s Pa), preferably of $1.5 \times 10^{-16}$ to $2 \times 10^{-16}$ kg/(m² s Pa). The melt viscosity MFR (melt flow rate) preferably lies between 40 and 65 g/10 minutes, preferably at 45-59 g/10 minutes and particularly preferably at 52 g/10 minutes.

In preferred versions the plastic is polyethylene, in particular polyethylene with a density between 900 and 1000 kg/m³. preferably between 960 and 970 kg/m³ (high-density polyethylene). Polycarbonate, polyester, polypropylene, polyethylene terephthalate, polyutethane are suitable. Poylethylene is preferred. Foamed plastics can also be used, for example those known e.g. by the brand names Hydrocerol®. These materials are plastics which are expanded during the processing (injection-moulding) by added or released foaming agents. Azodicarbonamide (ADC), 4,4'-oxybis(benzenesulfonylhydrazide) (BSH), 5-phenyltetrazole (5-PT), p-tuluylsulfonylsemicarbazide (TSS), p-tuluylsulfonylhydrazide (TSH), various citrates, citric acid, carbonates such as sodium dicarbonate and other foaming agents known from the state of the art for example can be used as foaming agents.

In a preferred version the top and the body have the form of a cylinder open on one side with round cross-section and a convex, virtually-hemispherical closed other side (lower part) and both consist of high-density polyethylene with a density between 950 and 1000 kg/m³.

The capsule sizes are matched to the respective inhalers. Examples of capsule dimensions are:

Length of the capsule body: from approx. 22 to approx. 9 mm, preferably: 22.2±0.46 mm; 20.22±0.46 mm; 20.98±0.46 mm; 18.4±0.46 mm; 16.61±0.46 mm; 15.27±0.46 mm; 13.59±0.46 mm; 13.1±0.1 mm; 12.19±0.46 mm; 9.3±0.46 mm.

Length of the capsule top: from approx. 13 to 6 mm, approx. preferably: 12.95±0.46 mm; 11.74±0.46 mm; 11.99±0.46 mm; 10.72±0.46 mm; 9.78±0.46 mm; 8.94±0.46 mm; 8.54±0.1 mm; 8.08±0.46 mm; 7.21±0.46 mm; 6.2±0.46 mm.

Outer diameter of the capsule bodies: from approx. 10 to approx. 4 mm, preferably: 9.55 mm; 8.18 mm; 7.36 mm; 7.34 mm; 6.63 mm; 6.07 mm; 5.57±0.06 mm; 5.05 mm; 4.68 mm.

Outer diameter of the capsule tops: from approx. 10 to approx. 4 mm, preferably: 9.91 mm; 8.53 mm; 7.66 mm; 7.64 mm; 6.91 mm; 6.35 mm; 5.83±0.06 mm; 5.32 mm; 4.91 mm.

Overall length of the closed capsule: from approx. 27 to approx. 11 mm, preferably: 26.1±0.3 mm; 23.3±0.3 mm; 24.2±0.3 mm; 21.7±0.3 mm; 19.4±0.3 mm; 18.0±0.3 mm; 15.9±0.3 mm; 14.3±0.3 mm; 11.1±0.3 mm.

Capsule capacities: from approx. 1.4 to approx. 0.1 ml, preferably: 1.37 ml; 0.95 ml; 0.78 ml; 0.50 ml; 0.37 ml; 0.30 ml; 0.24 ml; 0.21 ml; 0.13 ml.

Weight of the capsules: from approx. 170 mg to approx. 20 mg, preferably between 80 and 125 mg, preferred single values: 163 mg; 118 mg; 110 mg; 105 mg, 100 mg, 96 mg; 76 mg; 61 mg; 48 mg; 38 mg; 28 mg.

According to the invention, tops and bodies which as two complementary components can be inserted into each other via their open sides are provided with a pre- and main closure.

The pre-closure consists of a first channel running peripherally in the area of the opening round the outer casing of the capsule body as a ring, and a first raised section peripherally running round the inner casing of the capsule top also in the area of its opening as a ring, which is optionally segmented. The channel and the raised section fit into each other like a tongue and groove.

The following details relating to sizes preferably refer to a size 3 capsule. This is characterized by: length of the capsule body: 13.1±0.1 mm, length of the capsule top: 8.54±0.1 mm, total length of the capsule: 15.9±0.3 mm, outer diameter of the body: 5.57±0.06 mm, outer diameter of the top: 5.83±0.06 mm.

The channel preferably has a depth of 0.03 to 0.1 mm, particularly preferably 0.05 to 0.08 mm, more preferably 0.065 mm. Its width is preferably 0.1 to 0.25 mm, preferably 0.15 to 0.2 mm, particularly 0.18 mm.

The raised section is 0.04 to 0.08 mm, preferably 0.06 mm, high. It is not therefore necessary for the pre-closure for the spring part to completely fill the groove part. The raised section can be segmented. The raised section is 0.2 to 0.8 mm, preferably 0.3 to 0.6 mm, wide.

The segmentation can alternatively only be formed on the raised ring and e.g. be formed as a chain of punctiform raised sections, apart from a single punctiform raised section. A part-segmentation into three segments which are interrupted by non-raised part areas may be preferred. The segments are preferably 4 mm long. The non-raised part areas are preferably 1.3 mm long. The length of the segments can, however, naturally be chosen freely, whereby the force with which the segments sit in the complementary channels can be controlled. Here, length means the extension of the segment perpendicular to the width. The width is the extension parallel to the middle axis which points from the opening of the capsule element (top or body) to the closed end. Alternative versions with at least one or two punctiform segments of shorter length are indicated in the Figures.

The final closure (main closure) also consists of the first channel peripherally running round the outer casing of the capsule body as a ring, as already described in connection with the pre-closure, and a second raised section peripherally running round the inner casing lying behind the first raised section, seen from the opening, which can also optionally be segmented. The channel and the raised section fit into each other like a tongue and groove. Here, too, it is not necessary for the tongue part to completely fill the groove part.

The second raised section is 0.08 to 0.13 mm, preferably 0.10-0.11 mm, high. The raised section is 0.2 to 0.8 mm, preferably 0.3 to 0.6 mm, wide.

It is important that this second raised section is formed such that it completely fills the channel, thus offers more friction surface than the first raised section. For this, the second raised section can be less segmented, given the same height and width, it can be higher or wider than the first, or there is a combination of these variants. It is, however, important that the second raised section can also be completely occupied by the complementary channel at the other part-element of the capsule. The second raised section is preferably higher than the first raised section. The pre-closure is preferably designed such that the force needed to open by pulling the two capsule elements (top and body) apart lies between 0.1 and 3 N, preferably up to 2.5 N. The main closure can preferably not be opened by pulling apart without destroying it, at least the expenditure of force necessary for opening being higher than the up to 3 N for opening the pre-closure.

In order that the first raised section does not stand on the casing of the capsule top when the second raised section locks in the first channel, a second annular channel is formed behind the first channel (seen from the direction of the opening), whose measurements can correspond to those of the first channel. However, this second channel is preferably 0.02-0.09 mm, particularly preferably 0.05-0.06 mm, deep. It is preferably 0.1 to 0.25 mm, preferably 0.1 to 0.15 mm, in particular 0.13 mm, wide.

The raised sections can also be formed on the outer casing of the capsule body and the channels on the inner casing of the capsule top.

In a further version a bead is also formed on the outside of the body, running around the body perpendicular to the connection axis between top and body. The bead serves as a stopper for the capsule if this is fitted over the body, in order to prevent the top being pierced by the body. The area between the open end of the body and the bead corresponds to the area of the body over which the top can be pushed. The bead is located on the body such that the top can be pushed far enough over the body that the closure means can catch as described. Accordingly the bead is located behind the second annular channel or raised section. The side of the bead which faces the open end of the body stands as a perpendicular edge on the outer wall of the body such that the top cannot be pushed away over the bead upon closure. The side of the bead which points to the closed end of the body can be formed in the form of a virtually rectangular edge or flatten towards the closed end of the body. The formation of a virtually rectangular edge can be advantageous in the case of a loose fitting of the capsule in a capsule holder, the variant with flattening bead in the case of a firm fitting. The bead can be continuous or interrupted.

In a preferred version the bead flattens continuously towards the closed end of the body and stands perpendicular on the capsule body with its side oriented to the open end of the body. The height of the thus-formed edge is such that the edge does not project over the capsule top when closed. The transition from capsule top to capsule body can be plane but is preferably offset, i.e. the outer diameter of the top is larger than the greatest outer diameter of the body, or bead respectively.

The thickness of the walls of the top and of the body can vary over the entire area. Thus the thickness of the wall is generally greater in the rounded areas of the top or of the body or at the spot on the body at which the bead is formed greater than it is in the areas in which the walls run in a straight line. In one version, the walls of the top and of the body are 0.1 mm to 0.5 mm thick.

In one possible version burls are formed on the visible outside of the closed capsule, in another three or more ribs which run parallel to the longitudinal axis of the capsule. The advantage of these elements is that the capsule can be removed from a capsule holder, such as can e.g. be used in the above-named powder inhalers, without being damaged or opening. Optionally the ribs can also be formed as circumferential, spiral raised sections.

Further external design possibilities for the capsule can be found in the state of the art.

In order to obtain a better sealing between top and body when the capsule is closed the seam between top and body fuses can be heat-sealed, glued or bandrolled, the water vapour permeability thereby reducing to up to one tenth. Alternatively the whole top can be covered with a continuous protective film. Methods of heat-sealing the plastic capsule are disclosed in EP 1414639. Such methods include heat-sealing by means of laser, hot air, soldering iron etc.

In a further preferred version the gap can be heat-sealed with a filler. Pharmaceutically permissible filling materials are suitable as filler for such a filling of the gap.

Optionally it may be desired to inscribe the outer casing of the capsule. This can take place by customary inscription by means of inkjet printing and the like. As an alternative to this the inscription can also be applied afterwards by engraving or the inscription will be worked into the injection mould as an engraving or relief. In the latter case the inscription surface provided therefor can be flattened or otherwise raised. The engraved or relief-type characters can for their part be formed as a channel or raised section of e.g. 20 micrometers on the surface. The inscription can optionally be formed on the upper part or on the lower part or both elements, the inscription is preferably formed only on the lower part. By structuring the letters, numbers or symbols differently the capsule can be provided with information as regards contents or origin.

It is clear from the description that the capsule according to the invention is suitable for housing pharmaceutical formulations in powder form and suitable for inhalation. In a particular use form the capsule contains at least one of the active ingredients listed below or optionally combinations thereof:

Analgesics, antiallergics, anticholinergics, (antimuscarinics), antihistamines, antiinfectives, antitussives, betamimetics, bronchodilators, EGFR inhibitors, LTD4 antagonists, PDE-IV inhibitors, steroids etc.

Examples of analgesics are:

Codeine, dihydromorphine, ergotarnine, fentanyl. morphine; diltiazem.

Examples of antiallergics/antihistamines are:

Cromoglycate, sodium eromoglycate, epinastine, ketotifen, nedocromil, methapyrilene.

Examples of anticholinergics are:

Tiotropium salts, oxitropium salts, flutropium salts, ipratropium salts, glycopyrronium salts, trospium salts, there preferably being contained as counterion (anion) in each case chloride, bromide, iodide, sulphate, phosphate, methanesulphonate, nitrate, meleate, acetate, citrate, fumarate, tartrate, oxalate, succinate, benzoate or p-toluenesulphonate.

Ipratropium bromide, oxitropium bromide, tiotropium bromide, tiotropium bromide-monohydrate, trospium chloroide are preferred in each case. The compounds can optionally also be used as solvates, e.g. hydrates.

Examples of antiinfectives are:

Cephalosporin, penicillins, streptomycin, sulphonamides, tetracyclines, pentamidine.

Examples of antitussives are noscapine; ambroxol.

Examples of betamimetics are:

Bambuterol, bitolterol, carbuterol, clenbuterol, fenoterol, formoterol, hexoprenaline, ibuterol, isoprenaline, metaproterenol, phenylephrine, pirbuterol, procaterol, reproterol, salbutamol, (as a free base or sulphate), salmeterol, sulphonterol, terbutaline, tolubuterol, 4-hydroxy-7-[2-{[2-{[3-(2-phenylethoxy)propyl]sulphonyl}ethyl]-amino}ethyl]-2 (3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloroo-5-trifluoromethylphenyl)-2-tert.-butylarnino)ethanol or 1-(4-ethoxycarbonylamino-3-cyano-5-fluorophenyl)-2-(tert.-butylamino)ethanol.

Examples of EGFR inhibitors are:

4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluorophenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluorophenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluorophenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluorophenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methylamino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino)-7-cyclopropylmethoxy-quinazoline, 4-[(R)-(1-phenyl-ethyl)amino]-6-({4-[N-(2-methoxy-ethyl)-N-ethylamino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methylamino]-1-oxo-2-buten-1-yl}amino)-7-cyclopropylmethoxy-quinazoline, 4-[(R)-(1-phenyl-ethyl)amino]-6-({4-[N-(tetrahydrofuran-4-yl)-N-methylamino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methylamino]-1-oxo-2-buten-1-yl}amino)-7-cyclopentyloxy-quinazoline, 4-[(3-chloro-4-fluorophenyl)amino]-6-{[4-(N-cyclopropyl-N-methylamino)-1-oxo-2-buten-1-yl]amino}-7-cyclopentyloxy-quinazoline, 4-[(3-chloro-4-fluorophenyl)amino]-6-({4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethinyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-chinolin, 4-{[3-chloro-4-(3-fluoro-benzyloxy)-phenyl]amino}-6-(5-{[(2-methanesulphonyl-ethyl)amino]methyl}-furan-2-yl) quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethinyl-phenyl)amino]-6-{[4-(5,5-dimethyl-2-oxo-morpholin-4-yl)-1-oxo-2-buten-1-yl]amino}-quinazoline, 4-[(3-chloro-4-fluorophenyl)amino]-6-[2-(2,2-dimethyl-6-oxo-morpholin-4-yl)-ethoxy]-7-methoxy-quinazoline, 4-[(3-chloro-4-fluorophenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluorophenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluorophenyl)amino]-6-{2-[4-(2-oxo-morpholin-4-yl)-piperidine-1-yl]-ethoxy}-7-methoxy-quinazoline, 4-[(3-chloro-4-fluorophenyl)amino]-6-[1-(tert.-butyloxycarbonyl)-piperidine-4-yloxy]-7-methoxy-quinazoline, 4-[(3-chloro-4-fluorophenyl)amino]-6-(trans-4-amino-cyclohexane-1-yloxy)-7-methoxy-quinazoline, 4-[(3-chloro-4-fluorophenyl)amino]-6-(trans-4-methanesulphonylamino-cyclohexane-1-yloxy)-7-methoxy-quinazoline, 4-[(3-chloro-4-fluorophenyl)amino]-6-(tetrahydrofuran-3-yloxy)-7-methoxy-quinazoline, 4-[(3-chloro-4-fluorophenyl)amino]-6-(1-methyl-piperidine-4-yloxy)-7-methoxy-quinazoline, 4-[(3-chloro-4-fluorophenyl)amino]-6-{1-[(morpholin-4-yl)carbonyl]-piperidine-4-yloxy}-7-methoxy-quinazoline, 4-[(3-chloro-4-fluorophenyl)amino]-6-{1-[(methoxymethyl)carbonyl]-piperidine-4-yloxy}-7-methoxy-quinazoline, 4-[(3-chloro-4-fluorophenyl)amino]-6-(piperidine-3-yloxy)-7-methoxy-quinazoline, 4-[(3-chloro-4-fluorophenyl)amino]-6-[1-(2-acetylamino-ethyl)-piperidine-4-yloxy]-7-methoxy-quinazoline, 4-[(3-chloro-4-fluorophenyl)amino]-6-(tetrahydrofuran-4-yloxy)-7-ethoxy-quinazoline, 4-[(3-chloro-4-fluorophenyl)amino]-6-((S)-tetrahydrofuran-3-yloxy)-7-hydroxy-quinazoline, 4-[(3-chloro-4-fluorophenyl)amino]-6-(tetrahydrofuran-4-yloxy)-7-(2-methoxy-ethoxy)-quinazoline, 4-[(3-chloro-4-fluorophenyl)amino]-6-1trans-4-[(dimethylamino)sulphonylamino]- cyclohexane-1-yloxy}-7-methoxy-quinazoline, 4-[(3-chloro-4-fluorophenyl)amino]-6-1trans-4-[(morpholin-4-yl)carbonylamino]-cyclohexane-1-yloxy)-7-methoxy-quinazoline, 4-[(3-chloro-4-fluorophenyl)amino]-6-{trans-4-[(morpholin-4-yl)sulphonylamino]-cyclohexane-1-yloxy}-7-methoxy-quinazoline, 4-[(3-chloro-4-fluorophenyl)amino]-6-(tetrahydrofuran-4-yloxy)-7-(2-acetylamino-ethoxy)-quinazoline, 4-[(3-chloro-4-fluorophenyl)amino]-6-(tetrahydrofuran-4-yloxy)-7-(2-methanesulphonylamino-ethoxy)-quinazoline, 4-[(3-chloro-4-fluorophenyl)amino]-6-{1-[(piperidine-1-yl)carbonyl]-piperidine-4-yloxy}-7-methoxy-quinazoline, 4-[(3-chloro-4-fluorophenyl)amino]-6-(1-aminocarbonylmethyl-piperidine-4-yloxy)-7-methoxy-quinazoline, 4-[(3-chloro-4-fluorophenyl)amino]-6-(cis-4-{N-[(tetrahydrofuran-4-yl)carbonyl]-N-methylamino)-cyclohexane-1-yloxy)-7-methoxy-quinazoline, 4-[(3-chloro-4-fluorophenyl)amino]-6-(cis-4-{N-[(morpholin-4-yl)carbonyl]-N-methylamino}-cyclohexane-1-yloxy)-7-methoxy-quinazoline, 4-[(3-chloro-4-fluorophenyl)amino]-6-(cis-4-1N-[(morpholin-4-yl)sulphonyl]-N-methylamino}-cyclohexane-1-yloxy)-7-methoxy-quinazoline, 4-[(3-chloro-4-fluorophenyl)amino]-6-(trans-4-ethanesulphonylamino-cyclohexane-1-yloxy)-7-methoxy-quinazoline, 4-[(3-chloro-4-fluorophenyl)amino]-6-(1-methanesulphonyl-piperidine-4-yloxy)-7-ethoxy-quinazoline, 4-[(3-chloro-4-fluorophenyl)amino]-6-(1-methanesulphonyl-piperidine-4-yloxy)-7-(2-methoxy-ethoxy)-quinazoline, 4-[(3-chloro-4-fluorophenyl)amino]-6-[1-(2-methoxy-acetyl)-piperidine-4-yloxy]-7-(2-methoxy-ethoxy)-quinazoline, 4-[(3-chloro-4-fluorophenyl)amino]-6-(cis-4-acetylamino-cyclohexane-1-yloxy)-7-methoxy-quinazoline, 4-[(3-ethinyl-phenyl)amino]-6-[1-(tert.-butyloxycarbonyl)-piperidine-4-yloxy]-7-methoxy-quinazoline, 4-[3-ethinyl-phenyl)amino]-6-(tetrahydrofuran-4-yloxy)-7-methoxy-quinazoline, 4-[(3-chloro-4-fluorophenyl)amino]-6-(cis-4-{N-[(piperidine-1-yl)carbonyl]-N-methylamino}-cyclohexane-1-yloxy)-7-methoxy-quinazoline, 4-[(3-chloro-4-fluorophenyl)amino]-6-(cis-4-{1N-[(4-methyl-piperazin-1-yl)carbonyl]-N-methylamino}-cyclohexane-1-yloxy)-7-methoxy-quinazoline, 4-[(3-chloro-4-fluorophenyl)amino]-6-1cis-4-[(morpholin-4-yl)carbonylamino]-cyclohexane-1-yloxy}-7-methoxy-qunoinazoine, 4-[(3-chloro-4-fluorophenyl)amino]-6-{1-[2-(2-oxopyrrolidine-1-yl)ethyl]-piperidine-4-yloxy}-7-methoxy-quinazoline, 4-[(3-chloro-4-fluorophenyl)amino]-6-{1-[(morpholin-4-yl)carbonyl]-piperidine-4-yloxy}-7-(2-methoxy-ethoxy)-quinazoline, 4-[(3-ethinyl-phenyl)amino]-6-(1-acetyl-piperidine-4-yloxy)-7-methoxy-quinazoline, 4-[(3-ethinyl-phenyl)amino]-6-(1-methyl-piperidine-4-yloxy)-7-methoxy-quinazoline, 4-[(3-ethinyl-phenyl)amino]-6-(1-methanesulphonyl-piperidine-4-yloxy)-7-methoxy-quinazoline, 4-[(3-chloro-4-fluorophenyl)amino]-6-(1-methyl-piperidine-4-yloxy)-7(2-methoxy-ethoxy)-quinazoline, 4-[(3-chloro-4-fluorophenyl)amino]-6-(1-isopropyloxycarbonyl-piperidine-4-yloxy)-7-methoxy-quinazoline, 4-[(3-chloro-4-fluorophenyl)amino]-6-(cis-4-methylamino-cyclohexane-1-yloxy)-7-methoxy-quinazoline, 4-[(3-chloro-4-fluorophenyl)amino]-6-{cis-4-[N-(2-methoxy-acetyl)-N-methylamino]-cyclohexane-1-yloxy}-7-methoxy-quinazoline, 4-[(3-ethinyl-phenyl)amino]-6-(piperidine-4-yloxy)-7-methoxy-quinazoline, 4-[(3-ethinyl-phenyl)amino]-6-[1-(2-methoxy-acetyl)-piperidine-4-yloxy]-7-methoxy-quinazoline, 4-[(3-ethinyl-phenyl)amino]-6-{1-[(morpholin-4-yl)carbonyl]-piperidine-4-yloxy}-7-methoxy-quinazoline, 4-[(3-chloro-4-fluorophenyl)amino]-6-{1-[(cis-2,6-dimethyl-morpholin-4-yl)carbonyl]-piperidine-4-yloxy}-7-methoxy-quinazoline, 4-[(3-chloro-4-fluorophenyl)amino]-6-{1-[(2-methyl-morpholin-4-yl)carbonyl]-piperidine-4-yloxy}-7-methoxy-quinazoline, 4-[(3-chloro-4-fluorophenyl)amino]-6-{1-[(S,S)-(2-oxa-5-aza-bicyclo[2.2.1]hept-5-yl)carbonyl]-piperidine-4-yloxy}-7-methoxy-quinazoline, 4-[(3-chloro-4-fluorophenyl)amino]-6-{1-[(N-methyl-N-2-methoxymethyl-amino)carbonyl]-piperidine-4-yloxy }-7-methoxy-quinazoline, 4-[(3-chloro-4-fluorophenyl)amino]-6-(1-ethyl-piperidine-4-yloxy)-7-methoxy-quinazoline, 4-[(3-chloro-4-fluorophenyl)amino]-6-{1-[(2-methoxymethyl)carbonyl]-piperidine-4-yloxy}-7-methoxy-quinazoline, 4-[(3-chloro-4-fluorophenyl)amino]-6-{1-[(3-methoxypropyl-amino)-carbonyl]-piperidine-4-yloxy}-7-methoxy-quinazoline, 4-[(3-chloro-4-fluorophenyl)amino]-6-[cis-4-(N-methanesulphonyl-N-methylamino)-cyclohexane-1-yloxy]-7-methoxy-quinazoline, 4-[(3-chloro-4-fluorophenyl)amino]-6-[cis-4-(N-acetyl-N-methylamino)-cyclohexane-1-yloxy]-7-methoxy-quinazoline, 4-[(3-chloro-4-fluorophenyl)amino]-6-(trans-4-methylamino-cyclohexane-1-yloxy)-7-methoxy-quinazoline, 4-[(3-chloro-4-fluorophenyl)amino]-6-[trans-4-(N-methanesulphonyl-N-methylamino)-cyclohexane-1-yloxy]-7-methoxy-quinazoline, 4-[(3-chloro-4-fluorophenyl)amino]-6-(trans-4-dimethylamino-cyclohexane-1-yloxy)-7-methoxy-quinazoline, 4-[(3-chloro-4-fluorophenyl)amino]-6-(trans-4-{N-[(morpholin-4-yl)carbonyl]-N-methylamino}-cyclohexane-1-yloxy)-7-methoxy-quinazoline, 4-[(3-chloro-4-fluorophenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluorophenyl)amino]-6-(1-methanesulphonyl-piperidine-4-yloxy)-7-methoxy-quinazoline, 4-[(3-chloro-4-fluorophenyl)amino]-6-(1-cyano-piperidine-4-yloxy)-7-methoxy-quinazoline, cetuximab, trastuzumab, ABX-EGF and Mab ICR-62, optionally in the form of their racemates, enantiomers or diastereomers, optionally in the form of their pharmacologically compatible acid addition salts, their solvates and/or hydrates.

Examples of LTD4 antagonist are:

Montelukast, 1-(((R)-(3-(2-(6,7-difluoro-2-quinolinyl)ethenyl)phenyl)-3-(2-(2-hydroxy-2-propyl)phenyl)thio)methylcyclopropene-acetic acid, 1-(((1(R)-3(2-(2,3-dichlorothieno[3,2-b]pyridine-5-yl)-(E)-ethenyl)phenyl)-3-(2-(1-hydroxy-1-methylethyl)phenyl)propyl)thio)-methyl)-cyclopropane-acetic acid, pranlukast, zafirlukast, [2-[[2-(4-tert-butyl-2-thiazolyl)-5-benzofuranyl]oxymethyl]phenyl]acetic acid, MCC-847 (ZD-3523), MN-001, MEN-91507 (LM-1507), VUF-5078, VUF-K-8707 and L-733321, optionally in the form of their racemates, enantiomers or diastereomers, optionally in the form of their pharmacologically compatible acid addition salts as well as optionally in the form of their salts and derivatives, their solvates and/or hydrates.

Examples of PDE-IV inhibitors are:

from enprofylline, theophylline, roflumilast, ariflo (cilomilast), CP-325,366, BY343, D-4396 (Sch-351591), AWD-12-281 (GW-842470), N-(3,5-dichloro-1-oxo-pyridine-4-yl)-4-difluoromethoxy-3-cyclopropylmethoxybenzamide, NCS-613, pumafentine, (−)p-[(4aR*, 10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothiourea]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3- cyclopropylmethoxy-4-difluoromethoxyphenyl)cyclohexane-1-one, cis[4-cyano-4-(3-cyclopropylmethoxy-4-difluoromethoxyphenyl)cyclohexane-1-ol], (R)-(+)-ethyl[4-(3-cyclopentyloxy-4-methoxyphenyl)pyrrolidine-2-ylidene]acetate, (S)-(−)-ethyl[4-(3-cyclopentyloxy-4-methoxyphenyl)pyrrolidine-2-ylidene]acetate, CDP840, Bay-198004, D-4418, PD-168787, T-440, T-2585, arofylline, atizoram, V-11294A, Cl-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, and optionally in the form of their racemates, enantiomers or diastereomers, and optionally in the form of their pharmacologically compatible acid addition salts, solvates and/or hydrates.

Examples of steroids are:

Prednisolone, prednisone, butixocortpropionate, RPR-106541, flunisolide, beclomethasone, beclomethasone-17, 21-dipropionate, betamethasone valerate, betamethasone adamantoate, triamcinolone, budesonide, flunisolide, fluticasone, fluticasone propionate, mometasone, mometasone furoate, ciclometasone, ciclesonide, deflazacort, rofleponide, ST-126, dexamethasone, dexamethasone-21-isonicotinate, dexa-methasonisonicotinate, 6alpha,9alpha-difluoro-17alpha-[(2-furanylcarbonyl)oxy]-11beta-hydroxy-16alpha-methyl-3-oxo-androsta-1,4-dien-17beta-monothiocarboxylic acid (S)-fluoromethyl ester and 6alpha,9alpha-difluoro-11beta-hydroxy-16alpha-methyl-3-oxo-17alpha-propionyloxy-androsta-1,4-dien-17beta-monothiocarboxylic acid (S)-(2-oxo-tetrahydro-furan-3S-yl)ester, optionally in the form of their racemates, enantiomers or diastereomers and optionally in the form of their salts and derivatives, their solvates and/or hydrates.

Anticholinergics, in particular tiotropium, are particularly preferred. The latter is particularly preferably present as tiotropiumbromide monohydrate. Therefore one aspect of the invention relates to blisters according to the invention containing tiotropiumbromide monohydrate.

The named active ingredients can also be used in the form of other pharmacologically compatible salts, addition products, solvates etc.

The invention is preferably used for containers with the named active ingredients or combinations, but is not limited to the named active ingredients.

For further protection from humidity or the like, the capsules filled with the medicinal substance formulations can be heat-sealed for storage in blisters, pockets or the like or stored in bottles and other containers. Blisters and pockets from aluminum foil or laminate films which preferably also have an aluminum layer are particularly suitable.

DESCRIPTION OF THE FIGURES

The Figures show preferred versions of the capsule according to the invention but are merely illustrative and do not limit the scope of the invention.

FIG. 1 shows a preferred version of the capsule body in lateral cross-section.

FIG. 2 shows a preferred version of the capsule top with segmented pre-closure in lateral cross-section.

FIG. 3 shows a preferred version of the capsule top with segmented pre-closure in lateral cross-section.

FIG. 4 shows a preferred version of the capsule top with a non-segmented pre-closure in lateral cross-section.

Figure 5:
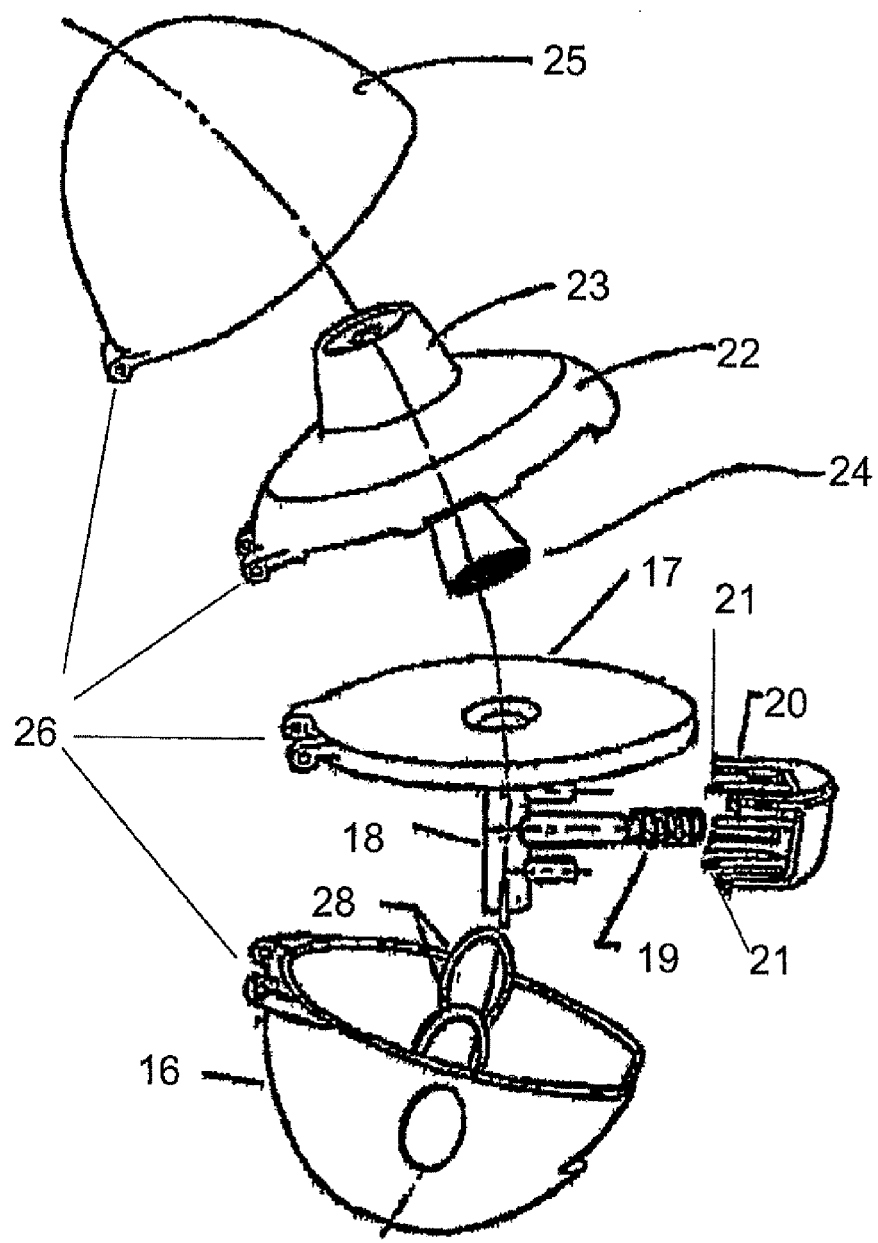
FIG. 5 shows the HandiHaler®.

A version of the capsule body according to the invention 1 is shown in cross-section in FIG. 1. The capsule body 1 has a convex lower part 2 and an opening 3. The first annular channel 5 running round peripherally is formed in the vicinity of the opening 3, and behind it the channel 6 with identical dimensions. Behind this is a bead 4 on which the opening of the capsule top 7 can lie when it is closed. Optionally a field 15 to which a letter code and/or numeric code can be applied, can be formed on the casing of the capsule lower part.

A version of the capsule top 7 is represented in FIG. 2. The top also has a convex lower part 8 and an opening 2. In the vicinity of the opening 2 the first annular raised section 11, running round peripherally but segmented, is formed, and behind it the raised section 10 non-identical in dimensions, annular, running round peripherally, but non-segmented, the main closure. The pre-closure is formed as an unbroken ring comprising three raised oblong segments 11 and three segments 12 lying between, formed planar with the casing of the top. The length of the raised segments—the length runs perpendicular to the top axis, the axis from the closed lower part to the opening—is greater than the length of the interrupting areas.

FIG. 3 shows a comparable version, in which only two segments in the form of punctiform raised sections 13 are formed.

Finally, a version is represented in FIG. 4 in which the pre-closure is also represented as continuous raised section 14. The latter is not identical in its dimensions with the raised section 10.

The represented capsule tops and the capsule body are not to scale relative to each other. In reality the two components fit together like complementary components.

FIG. 5 shows the HandiHaler® consisting of a) a cup-shaped lower part 16 open to the top, b) a panel 17 which covers the opening of the lower part and is formed perpendicular to the one capsule chamber 18, a burl 20 movable towards a spring 19 being provided at the capsule chamber 18, having two ground needles 21 for opening the capsule, c) an upper part 22 with a mouth tube 23 and an air inlet pipe with screen 24 via which the powder aerosol from the capsule chamber can be inhaled and d) a top 25. The elements a), b) c) and d) are thus joined to one another by a common hinge element 26 so that they can be moved foldable towards each other. The appliance can optionally have the inspection windows 28.

The invention claimed is:

1. A capsule, for use as reservoir for pharmaceutical preparations in powder inhalers, comprising two capsule elements each open on one side, the elements being a capsule body and a capsule top the relative sizes of the elements allowing them to be inserted telescopically into each other via their openings so that a stable, sealed cavity of defined volume is formed, wherein:

the capsule elements are of a non-water-soluble plastic material, two annular channels lying behind one another relative to the opening, running peripherally around a first capsule element are formed on the inside or outside of the first capsule element in the vicinity of its opening and two annular raised sections lying behind one another relative to the opening, running peripherally around the other capsule element are formed on the outside or inside of the other capsule element in the vicinity of its opening, provided that when the annular channels are formed on the inside of the first capsule element then the raised sections are formed on the outside of the other capsule element and the other capsule element fits inside the first capsule element and that when the annular channels are formed on the outside of the first capsule element then the raised sections are formed on the inside of the other capsule element and the first capsule element fits inside the other capsule element, and further provided that the raised section furthest from the opening is continuous around the capsule element and is higher and/or wider and/or has more surface area than the raised section closest to the opening and the raised section closest to the opening is optionally segmented, the raised sections and the annular channels being positioned correspondingly such that the two raised sections catch within the two annular channels upon the telescopic closure of the two capsule elements, the first raised section closest to the opening of the other capsule element and the first channel closest to the opening on the first capsule element, capable of forming a pre-seal of the elements when the first raised section catches within the first channel, the opening of which by pulling apart the two capsule elements requires a first force, and the second raised section furthest from the opening of the other capsule element and the first channel on the first capsule element capable of forming a main closure when they catch within each other, the opening of which by pulling apart the two capsule elements requires a second force, and the first force to be applied for opening is smaller than the second force.

2. The capsule according to claim 1, wherein the first force is up to 3 N.

3. The capsule according to claim 1, wherein when a main closure of the elements is formed it cannot be opened by pulling apart the capsule elements without destroying them.

4. The capsule according to claim 1, wherein the annular channels are formed on the outside of the capsule body and the raised sections are formed on the inside of the capsule top.

5. The capsule according to claim 1, wherein the depth of at least one annular channel is 0.03 to 0.1 mm.

6. The capsule according to claim 5, wherein the depth of the channel is 0.05-0.08 mm.

7. The capsule according to claim 5, wherein the depth of the channel is 0.065 mm.

8. The capsule according to claim 1, wherein the first raised section closest to the opening is 0.04 to 0.08 mm high.

9. The capsule according to claim 1, wherein the second raised section furthest from the opening is 0.08 to 0.13 mm high.

10. The capsule according to claim 1, wherein the capsule top and the capsule body have walls which are 0.1 mm to 0.5 mm thick.

11. The capsule according to claim 1, wherein the capsule elements are made of polyethylene, polycarbonate, polyester, polypropylene or polyethylene terephthalate.

12. A method comprising loading the capsule according to claim 1 containing a pharmaceutical preparation into a powder inhaler such that the pharmaceutical preparation is capable of being administered by inhalation using the inhaler.

13. The capsule according to claim 1, wherein at least one raised section is 0.06 mm high.

14. The capsule according to claim 1, wherein at least one raised section is 0.10-0.11 mm high.

15. The capsule according to claim 1, wherein both the raised section furthest from the opening and the raised section closest to the opening are continuous around the capsule element.

* * * * *